(12) United States Patent
Magnusson et al.

(10) Patent No.: US 8,419,704 B2
(45) Date of Patent: Apr. 16, 2013

(54) ABSORBENT ARTICLE WITH FASTENING FLAPS

(75) Inventors: Elinor Magnusson, Mölnlycke (SE);
Solgun Drevik, Mölnlycke (SE)

(73) Assignee: SCA Hygiene Products AB, Goteborg (SE)

( * ) Notice: Subject to any disclaimer, the term of this patent is extended or adjusted under 35 U.S.C. 154(b) by 554 days.

(21) Appl. No.: 12/597,501

(22) PCT Filed: Jun. 29, 2007

(86) PCT No.: PCT/SE2007/050482
§ 371 (c)(1),
(2), (4) Date: Oct. 26, 2009

(87) PCT Pub. No.: WO2009/005423
PCT Pub. Date: Jan. 8, 2009

(65) Prior Publication Data
US 2010/0087793 A1    Apr. 8, 2010

(51) Int. Cl.
*A61F 13/58* (2006.01)
(52) U.S. Cl.
USPC .......................................... 604/389; 604/386
(58) Field of Classification Search ........... 604/389–391
See application file for complete search history.

(56) References Cited

U.S. PATENT DOCUMENTS

| 5,133,706 A | * | 7/1992 | Dixon ........................... 604/389 |
| 5,281,209 A | | 1/1994 | Osborn, III et al. |
| 5,288,546 A | * | 2/1994 | Roessler et al. ............. 428/40.1 |
| 5,399,219 A | * | 3/1995 | Roessler et al. ............. 156/259 |
| 5,730,739 A | | 3/1998 | Lavash et al. |
| 5,926,926 A | * | 7/1999 | Kato .............................. 24/442 |

FOREIGN PATENT DOCUMENTS

| WO | WO 93/06805 A1 | 4/1993 |
| WO | WO 94/00091 A1 | 1/1994 |
| WO | WO 94/14398 A1 | 7/1994 |
| WO | WO 96/23469 A1 | 8/1996 |
| WO | WO 96/23472 A1 | 8/1996 |
| WO | WO 97/34555 A1 | 9/1997 |
| WO | WO 2004/019850 A1 | 3/2004 |

OTHER PUBLICATIONS

International Search Report (Form PCT/ISA/210) of PCT/SE2007/050482 dated Mar. 11, 2008.

* cited by examiner

*Primary Examiner* — Susan Su
(74) *Attorney, Agent, or Firm* — Buchanan Ingersoll & Rooney PC

(57) ABSTRACT

An absorbent article (1) includes an absorbent body (5) arranged superpositioned onto a backsheet (4). The absorbent article (1) has a side edge (6; 12a, 12b) encompassing the absorbent article (1). The absorbent article (1) includes at least one fastening tab (2) positioned along the side edge (6; 12a, 12b). In a first position the fastening tab (2) is folded over itself at least once creating at least one first pleat (13) and secured in its folded position by fastening means (17) positioned in the first pleat (13) on only a first side (14) of the fastening tabs (2), and in that in a second position, the fastening tab (2) is arranged to be unfolded at least partly for attachment to the outside and/or the inside of an undergarment (21).

25 Claims, 14 Drawing Sheets

ABSORBENT ARTICLE WITH FASTENING FLAPS

TECHNICAL FIELD

The invention relates to absorbent articles such as, for example, sanitary napkins, panty liners, diapers, male and female incontinence articles, etc. The absorbent article comprises an absorbent body arranged superpositioned onto a backsheet. The sanitary napkin has an extension in a longitudinal direction X and a lateral direction Y. The sanitary napkin has a front portion, a rear portion and a central portion therebetween. The sanitary napkin has a side edge encompassing the sanitary napkin. The sanitary napkin comprises two opposing fastening tabs each positioned along the longitudinally extending side edges.

BACKGROUND

In the field of absorbent articles it is known absorbent articles arranged to be worn in the genital area of a user in order to protect the undergarment from bodily fluids such as menstrual fluids and small amounts of urine, etc. Thin absorbent articles are known to be called sanitary napkins, sanitary towels, panty liners, etc. Common for all absorbent articles is that they comprise an absorbent body and a liquid impervious backsheet. Most absorbent article comprise a liquid pervious topsheet, a liquid impervious backsheet and an absorbent body therebetween. The absorbent article is positioned in the undergarment with the backsheet against the undergarment. It is common that the absorbent article comprises different fastening arrangements for securing the absorbent article to the undergarment. One type of fastening arrangement is adhesive positioned on the backsheet and arranged to be releasably attached to the undergarment when the absorbent article is positioned in the undergarment.

Another type of fastening arrangement is fastening tabs extending from the longitudinal side edges of the absorbent article and arranged to be folded over the side edges of the undergarment and to be attached to the outside of the absorbent article. The fastening tabs are often called wings or flaps due to its position and shape when they are in an unfolded state. Fastening tabs are known from WO 93/06805 and WO 94/00091 and the fastening means are fixedly attached to the backsheet by welding or the like, or the fastening means are part of the backsheet.

One problem with the previously known tabs is that they are restricted to a number of simple shapes (e.g. round) since some of the more advanced shapes of the tabs are regarded as aesthetically non-pleasing when the absorbent article is displayed for sale. A more advanced shape can give a better fastening of the absorbent article in the undergarment.

Hence, there exists a need for an absorbent article comprising an improved fastening tab.

SUMMARY

The invention refers to an absorbent article such as any thin absorbent article, for example sanitary napkins and panty liners, or any other type of absorbent articles, for example diapers, male and female incontinence articles. Common for all absorbent articles is that they are intended for use as an undergarment protection against menstrual fluids, urine during light incontinence, and protection against vaginal discharges that may soil the undergarment.

The absorbent article comprises an absorbent body superpositioned onto a backsheet. The absorbent article may also comprise a topsheet superpositioned onto the absorbent body on the opposite side of the backsheet. The absorbent article has an extension in a longitudinal direction and a lateral direction. The absorbent article is in the longitudinal direction divided into a front portion a rear portion and a central portion therebetween.

The absorbent article is in the lateral direction divided into two side sections and a mid section therebetween. The division of the absorbent article into portions and sections is of a theoretical nature and is intended to be used as an aid in the description of the absorbent article and shall not be seen as being limiting for the invention.

The absorbent article has a side edge encompassing the absorbent article. The side edge may be divided into two opposing longitudinally extending side edges and two laterally extending side edges the different side edges may have a curved shape or a straight shape. The topsheet may be folded over the side edge and/or the backsheet may be folded over the side edge. The topsheet and the backsheet may also be bonded together along the side edge forming a side seam. The side seam may also comprise parts of or the entire absorbent body. If the absorbent article comprises only an absorbent body and a backsheet, the side seam may be formed by bonding together at least a part of the absorbent body and the backsheet.

The absorbent article is characterized in that the fastening tab, in a first position, is folded over itself at least once creating at least one first pleat. The fastening tab is secured in its folded position by a fastening means positioned in the first pleat on a first side of the fastening tabs only.

Here "in the first pleat" means the space created between the subsidiary parts of the fastening tabs that are folded over each other. Hence, "a pleat" refers to two subsidiary parts of the fastening tab being folded over each other forming such a space.

Here "a first side of the fastening tab" refers to only one side of the fastening tab. The fastening flap may be arranged on the absorbent article such that the first side is positioned on the same side as the backsheet, hereinafter called the outside. The "same side" means that when the fastening flap is in an unfolded state, i.e. in an un-pleated state, and positioned in the same plane as the absorbent article, the first side faces in the same direction as the part referred to, i.e. here the backsheet. The first side may also be positioned on the same side as a top surface of the absorbent article, hereinafter called the inside. The top surface refers to an outwardly facing surface of a topsheet or an absorbent body. The top surface is positioned on the opposite side of the absorbent article with reference to the backsheet. The fastening tab also comprises a second side positioned on the opposite side of the first side.

In a second position, the fastening tabs are arranged to be unfolded at least partly so that the fastening means are revealed so that the fastening means can be attached to the inside and/or the outside of an undergarment. When the fastening means is positioned on the outside of the fastening flap the fastening means can be attached to the outside of an undergarment by folding the fastening flap over the edges of an undergarment.

However, when the fastening means is positioned on the outside of the fastening flap the fastening means can be attached to the inside of an undergarment, for example by not folding the fastening flap over the edges of an undergarment.

When the fastening means is positioned on the inside of the fastening flap the fastening means can be attached to the inside and/or the outside of an undergarment.

The position of the fastening means, i.e. on the inside or the outside of the fastening tab, together with the position of the fastening tabs in the absorbent article allows for different types of folding and attachment. The desired use of the fastening tab can thus be met by combining the position of the fastening tab in the absorbent article with the position of the fastening means and the way the tab is intended to be folded. This will be explained further below. Common for all embodiments are however that Preferably, the fastening tab should comprise fastening means on one side of the fastening tab only.

One advantage of the invention is that the fastening tab can have an aesthetically pleasing shape in the first position and a functionally perfect shape in the second position. A further advantage is that the pleat gives the possibility to arrange the fastening tab so that the user can arrange the fastening tabs in a number of different ways by manipulating the fastening tabs. Examples of this will be apparent in the below description of the invention.

The invention thus relates to an improved absorbent article comprising at least one fastening tab positioned along the side edge for attachment to the outside and/or the inside of an undergarment. The fastening flap may thus in its entirety be positioned inside or outside an undergarment or may be positioned partly inside and partly outside the undergarment.

When the fastening flap is arranged to be positioned inside an undergarment the flaps may comprise an absorbent material for extra leakage protection.

One fastening tab can, for example, be used in a men's undergarment. The fastening tab is then advantageously positioned in the front portion or the rear portion along the laterally extending side edge. The user may after insertion of the absorbent article into the undergarment bring the side flap from the first position into the second position and may then attach the fastening flaps on the outside and/or on the inside of the undergarment.

However, the absorbent article may comprise at least two fastening tabs positioned on either side of the absorbent article along the longitudinally extending side edges for improved fastening abilities. The fastening tab(s) may be positioned in the front portion or the rear portion or the central portion or at a position therebetween. Here "therebetween" refers to the transition zone between the different portions, i.e. a part of the fastening tab may be positioned in one portion and another part in another portion. The side flaps may be positioned at different locations along the side edge and need not be positioned opposite each other but may be positioned in a diagonal pattern with reference to a longitudinally extending center line of the absorbent article.

Furthermore, the two above described embodiments may be combined so that there are at least one fastening tab attached along one of the longitudinally extending side edges and at least one fastening tab attached to one of the laterally extending side edges.

The fastening means is advantageously an adhesive that bonds together the fastening tabs in the first position, but allows for the fastening tabs to be unfolded into the second position. The fastening means shall preferably separate into two essentially equal parts when the pleat is unfolded so that the fastening means cover essentially the entire surface described by the unfolded pleat. When the fastening tabs then are folded over the undergarment in the second position, the fastening means can adhere to the outside of the undergarment and/or the inside of the undergarment.

The fastening tabs may be folded over the side sections and may form side leakage barriers in the first position. The fastening tabs may be folded over the absorbent body side of the absorbent article or may be folded over the backsheet side of the absorbent article. In the first case when the fastening tabs are folded over the topsheet (or the absorbent body where applicable) the pleated fastening tabs themselves create side leakage barriers. In the second case where the fastening tabs are folded over the backsheet, the pleated fastening tabs indirectly form side leakage barriers by pushing the material in the absorbent article in direction towards the mid section during use. The "pushing" is a consequence of the user's body pushing onto the pleated fastening tabs during use since the pleated fastening tabs will be positioned between the undergarment and the absorbent article. In one embodiment of the invention, the fastening tabs are only partly unfolded, i.e. a part of the fastening tabs remains in the first position (i.e. in a folded position) and the unfolded parts in the second position are used for fastening the absorbent article in the undergarment.

The benefits of the invention become even more obvious when each fastening tab is folded over itself two times. The folding of the fastening tab then creates one first pleat on the first side of the fastening tabs and one second pleat on the second side of the fastening tab.

The second pleat may be filled at least partially with an additive. The additive may be a skincare lotion, an odour inhibitor, a medicament for the user, an absorbent material, or any other additive that can be to use in the absorbent article.

The benefits of the invention will be still more obvious if each fastening tab is folded over itself at least three times creating at least two first pleats on the first side of the fastening tabs and at least one second pleat on the second side of the fastening tab. In addition to the above described advantages, the two first pleats may comprise fastening means with different properties. For example, one of the first pleats may comprise a fastening means with a different adherent strength than a fastening means of another first pleat giving the fastening tab a selective and stepwise unfolding of the different pleats. This is advantageous since the user may chose to unfold only one, or more, of the first pleats. For example, the additional pleats may be kept along the side sections for side leakage protection when one or more unfolded pleats are used as fastening tabs on the first side of the undergarment. The fastening tabs may also comprise zones with different properties that allows for the fastening tabs to be formed when the fastening tabs are unfolded from the first position to the second position. The different strength of the fastening means may then bond together the subsidiary parts of the fastening tabs until the zone has changed form and the force upon the fastening means goes beyond a selected threshold level. It is here understood that the zones are arranged to change form when a certain shearing force is applied to the fastening tab which force is below the threshold level of the fastening means.

The fastening tabs may thus comprise a first zone and a second zone having different elastic properties for shaping the fastening tab when the fastening tab is brought from the first position to the second position. The first zone may be permanently and/or plastically deformable and the second zone may have the same or different properties.

The fastening tabs may comprise a reinforcement zone arranged to shape the fastening tab when the fastening tab is brought from the first position to the second position. The reinforcement zone may be in the form of a line or a group of lines, or a circle, or may have a rectangular shape, or oval shape or quadratic form or any polygon shape, for example triangular, pentagon etc. or a combination of the different shapes.

In another embodiment of the invention, the fastening tabs are detachably attached to the absorbent article. One benefit of this embodiment is that the fastening tabs are optional for the user, i.e. the user may separate the fastening tabs from the absorbent article should the user for any reason opt out the fastening tabs.

The fastening tabs may be detachably attached to the backsheet of the absorbent article or the fastening tabs may be detachably attached to the absorbent article via an adhesive.

In one embodiment the fastening tabs may be comprised in one tab sheet extending over the entire backsheet of the absorbent article. The tab sheet may be arranged as a release sheet for a first adhesive strip positioned on the backsheet so that the first adhesive strip is revealed should the tab sheet be removed. The tab sheet may also comprise a second adhesive strip positioned on the opposite side of the tab sheet in relation to the first adhesive strip. In the latter embodiment the absorbent article may comprise a release sheet for the second adhesive strip.

However, the fastening tab may be fixedly attached to the absorbent article and the fastening tab may be fixedly attached to the backsheet or the fastening tab may be an extension of the backsheet. In any of the above described embodiments, the fastening tab or the tab sheet tab may comprise a tear line comprising compressed zones, indentations or apertures, or the like arranged to weaken the tear line for allowing separation of the fastening tab from the absorbent article.

In one embodiment of the invention, the fastening tabs are positioned along the longitudinal side edges in the first position without being folded over the absorbent body. The fastening tabs may be brought from this first position to the second position according to the above.

The fastening means may be any adhesive or sticky material that can be delaminated partly or fully when the first pleats are unfolded so that the fastening means can be attached to the undergarment. Here "delaminated" means that the fastening means in one first pleat is separated into two parts covering the subsidiary parts of the fastening tab making up the first pleat. The fastening means shall also have a property that allows the fastening means to adhere to the undergarment when the fastening tab is secured against the undergarment, but allows for the fastening means to be removed from the undergarment essentially in its entirety when the fastening tab is removed from the undergarment. In one embodiment of the invention the fastening means may be arranged to not delaminate but to stick to one of the subsidiary layers upon unfolding of the first pleat.

BRIEF DESCRIPTION OF THE DRAWINGS

The invention will below be described in connection to a number of drawings, in which:

FIG. 13 schematically shows a top view of an absorbent article according to a fifth embodiment of the invention, and in which;

DETAILED DESCRIPTION

Figure 1:
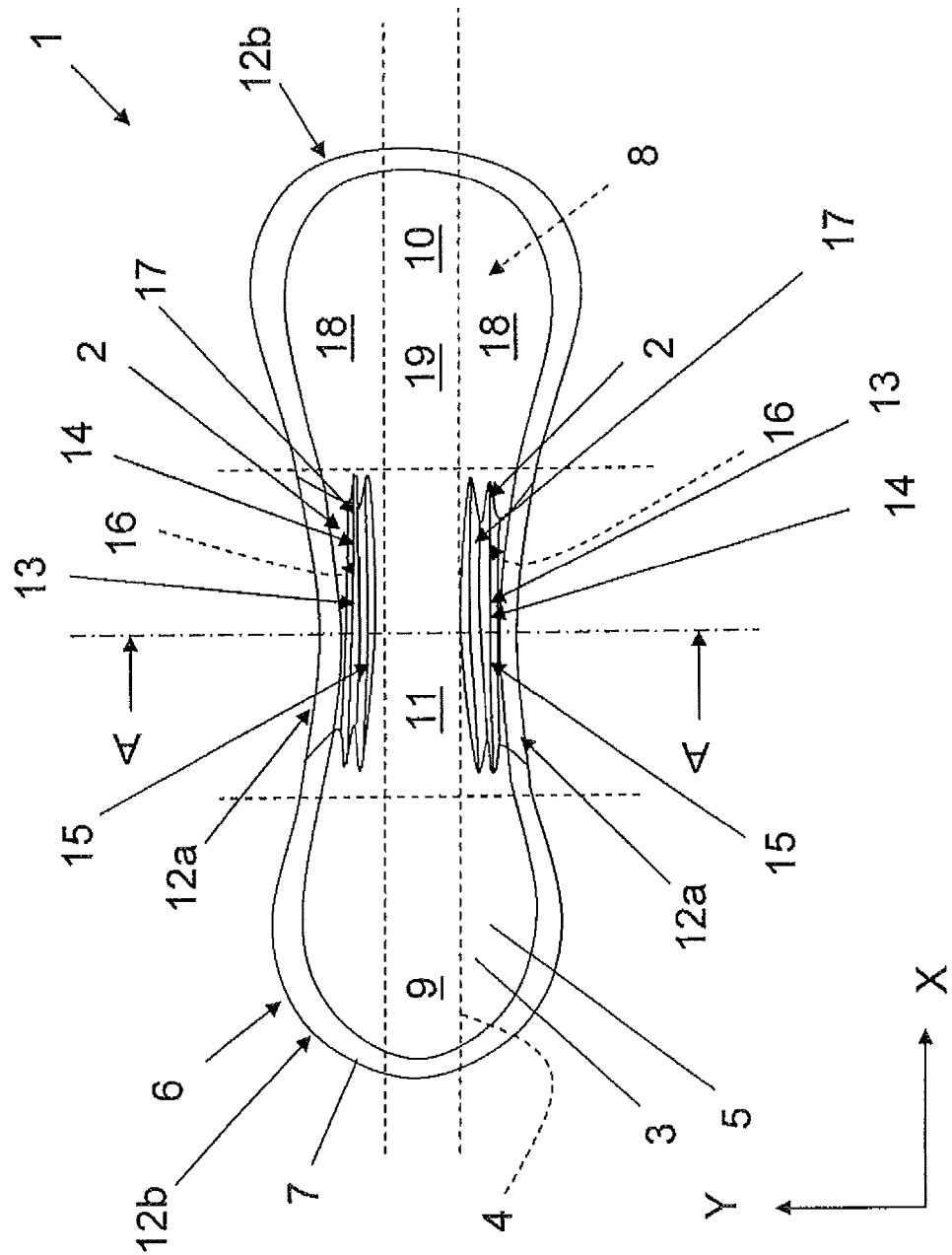
FIG. 1 schematically shows a top view of an absorbent article in a first position according to a first embodiment of the invention.

In the drawings the fastening tabs have been blown out of proportion in order to facilitate the description of the invention.

FIG. 1 schematically shows a top view of an absorbent article 1 in a first position according to a first embodiment of the invention. The first position refers to fastening tabs 2 being in a folded position. In FIG. 1, the absorbent article 1 comprises a topsheet 3, a backsheet 4 and an absorbent body 5 positioned between the topsheet 3 and the backsheet 4. In FIG. 1, the topsheet 3 is bonded to the backsheet 4 around a peripheral side edge 6. The bonding may be made by any known technique, for example ultrasonic welding, laser welding, mechanical pressure, heat welding, use of an adhesive, etc. The bonding may result in a side seam 7 extending around the peripheral side edge 6. The absorbent body 5 is enclosed within the volume created by the bonded together topsheet 3 and backsheet 4. However, the absorbent body 5 may be part of the side seam 7, i.e. e.g. a peripheral part of the absorbent body 5 may be positioned between the topsheet 3 and the backsheet 4 and may be bonded together with the topsheet 3 and the backsheet 4. The absorbent body 5 may comprise a number of layers (not shown) with different properties and any of or all of the layers may be comprised in the side seam 7.

The absorbent article 1 is not limited to the use of a topsheet 3, but the absorbent article 1 may comprise only an absorbent body 5. In the latter embodiment, a top surface 8 of the absorbent body 5 acts as a topsheet and may be treated for giving a soft feel to a user and may comprise apertures or any other suitable structure and material that allows for receiving and transporting liquid in a direction away from the body of the user.

In FIG. 1 the absorbent article 1 has an extension in a longitudinal direction X and a lateral direction Y. The absorbent article 1 has a front portion 9, a rear portion 10 and a central portion 11 therebetween. The peripheral side edge 6 is divided into two opposing longitudinally X extending side edges 12a and two opposing laterally Y extending side edges 12b. In FIG. 1 the absorbent article 1 comprises two opposing fastening tabs 2 each positioned along the longitudinally extending side edges 12a. Each fastening tab 2 is folded over itself a number of times creating a number of first pleats 13 positioned on a first side 14 of the fastening tab 2 and a number of second pleats 15 positioned on an second side 16 of the fastening tab 2. Here "first side of the fastening tabs" means that side of the fastening tabs 2 that faces away from the top sheet 3 should the fastening tabs 2 be positioned over the topsheet 3 side of the absorbent article 1 in an unfolded state. However, in another embodiment (not shown) the "first side of the fastening tabs" could mean that side of the fastening tabs 2 that faces towards the topsheet 3 should the fastening tabs 2 be positioned over the topsheet 3 side of the absorbent article 1 in an unfolded state. The number of pleats can vary from one first pleat 13 and no second pleats 15 to a number of first pleats 13 and a number of second pleats 15.

The fastening tab 2 is secured in its folded position by a fastening means 17 positioned in the first pleats 13 on the first side 14 of the fastening tabs 2. It is imperative for the invention that the fastening means 17 is positioned on the first side 14 of the fastening tab only since the fastening means 17 are arranged to bond to an undergarment (see FIG. 3). The fastening means 17 that are suitable for adhering to an undergarment is normally not suitable to be positioned against the body of a user since the fastening means 17 can affect the skin negatively or may stick to the pubic hair of the user which of course will be experienced as negative during use and when the absorbent article is about to be removed from the body. However, the benefit of having the fastening means 17 in the first pleats 13 is that the area that can adhere to the undergarment is increased when the fastening tabs are unfolded.

FIG. 1 shows that, in the lateral direction, the absorbent article is divided into two side sections 18 and a midsection 19 therebetween. In the first position, the fastening tabs 2 are folded over the side sections 18 respectively. FIG. 1 also shows that the fastening tabs are positioned in the central portion 11 along the curved longitudinally extending side edges 12a. The length, width and position of the fastening tabs 2 may vary within the scope of the claims and are not limited to the embodiments described in the figures. For example, the fastening tabs 2 may have an extension in the longitudinal direction that coincide with the longitudinal extension of the central portion 11 and a part of the longitudinal extension of the front portion 9 and or the rear portion 10. Furthermore, the fastening tab 2 may be positioned partly in the central portion 11 and partly in the front portion 9 or the rear portion 10. A number of different embodiments of the first position will be described in more detail below.

Figure 2:
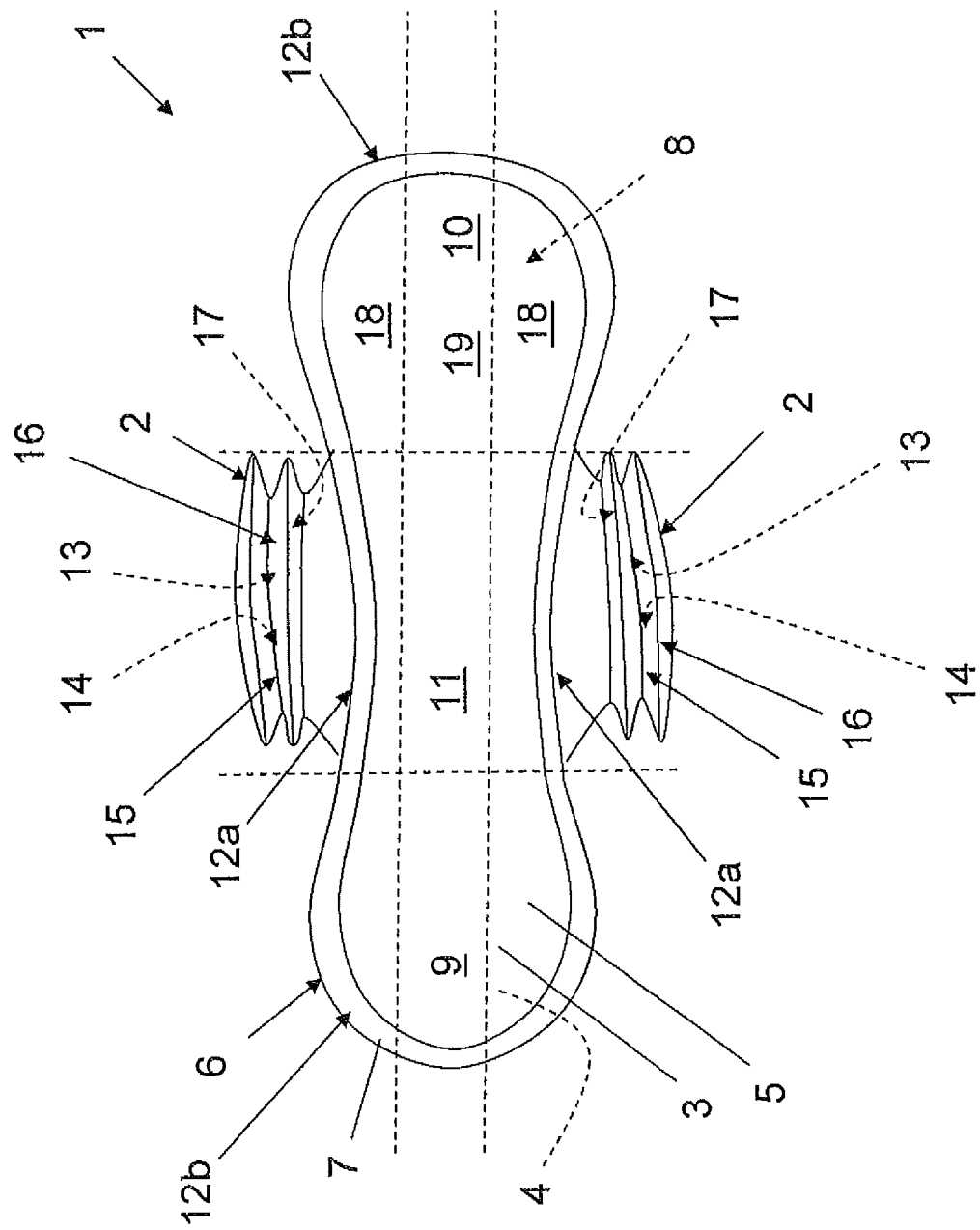
FIG. 2 schematically shows a top view of an absorbent article in a second position according to the first embodiment of the invention.

FIG. 2 schematically shows a top view of the absorbent article 1 in a second position according to the invention. The second position refers to a position where the fastening tabs 2 are unfolded at least partly so that the fastening means 17 can be attached to the outside of the undergarment. In FIG. 2, all pleats 13, 15 in the fastening tabs 2 are unfolded. However, the fastening means 17 may be arranged with different properties in different first pleats 13. This gives a possibility to unfold only a selected amount of first pleats 13 and second pleats 15 when the user applies a first level of force to the fastening tabs. The fastening means 17 may also be arranged so that additional first pleats 13 and second pleats 15 are unfolded when the force is increased to a second level of force.

Figure 11:
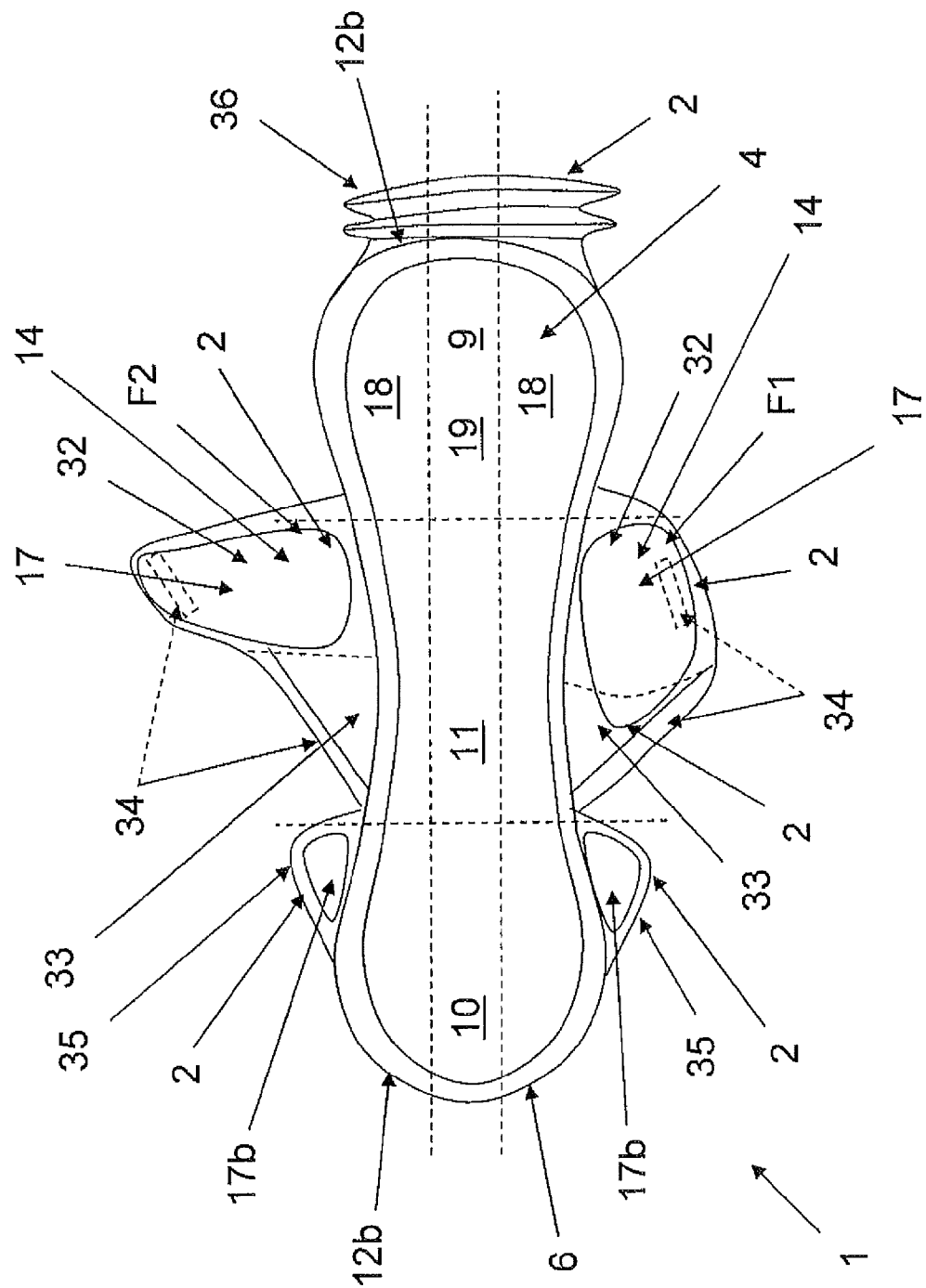
FIG. 11 schematically shows a top view of an absorbent article according to a third embodiment of the invention.

The fastening tabs may comprise a first zone and a second zone having different properties for shaping the fastening tabs 2 when the fastening tabs 2 are brought from the first position to the second position (see FIG. 11). The first zone and the second zone may have different elastic properties which gives the advantage that each fastening tab 2 may be formed into a predetermined shape. For example, the fastening tabs 2 may have an essentially rectangular shape in the first position, but may in the second position achieve a dramatically changed shape, for example banana shaped or in the shape of a parallelogram etc.

The first zone and/or the second zone may be permanently and/or plastically deformable. The first zone may have different properties than the second zone. Furthermore, in order to aid in the shaping of the fastening tab when brought from the first position to the second position, the fastening tab may comprise a reinforcement zone (see FIG. 11).

The fastening tabs 2 may also comprise gripping means (26, see FIG. 4) that the user can hold when arranging the fastening tabs 2 into a desired position or shape.

Figure 3:
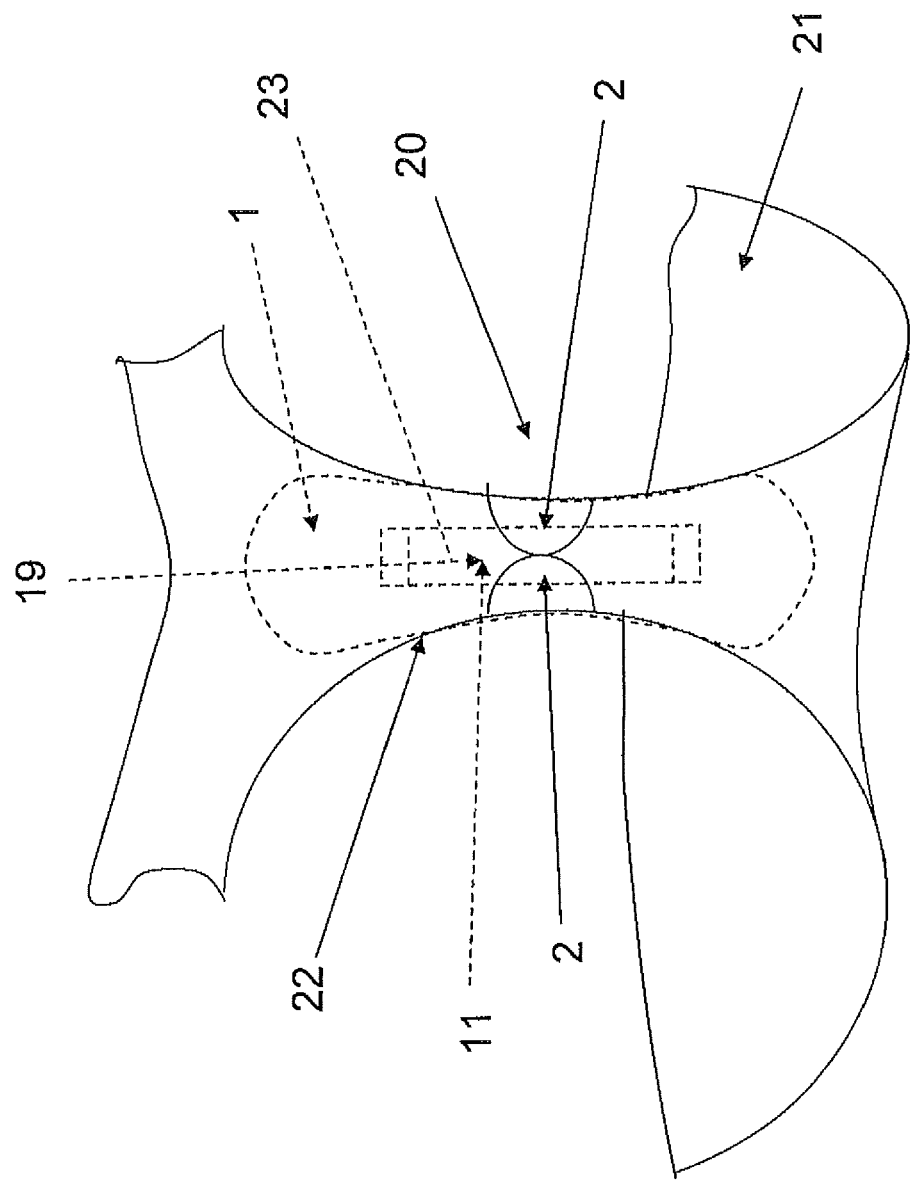
FIG. 3 schematically shows a perspective view of an absorbent article according to the invention positioned in an undergarment.

FIG. 3 schematically shows a perspective view of an absorbent article 1 according to the invention. The absorbent article 1 is positioned in a midsection 21 of an undergarment 21 and the fastening tabs 2 are folded around the edges 22 of the undergarment 21. In FIG. 3 it is shown that the absorbent article 1 comprises a fastening strip 23 positioned on the backsheet 4 of the absorbent article 1 in connection to the cross-section between the central portion 11 and the mid section 19 of the absorbent article 1. The fastening strip 23 is arranged to adhere to the inside of the undergarment 21 and cooperates with the fastening tabs 2 in holding the absorbent article 1 in position in the undergarment 21. In another embodiment of the invention, the fastening strip 23 may be opt out so that the fastening tabs 2 are the only devices for holding the absorbent article 1 in position. The fastening strip may 23 also be positioned in another location on the absorbent article 1 and may have any suitable geometrical shape or pattern.

Figure 4:
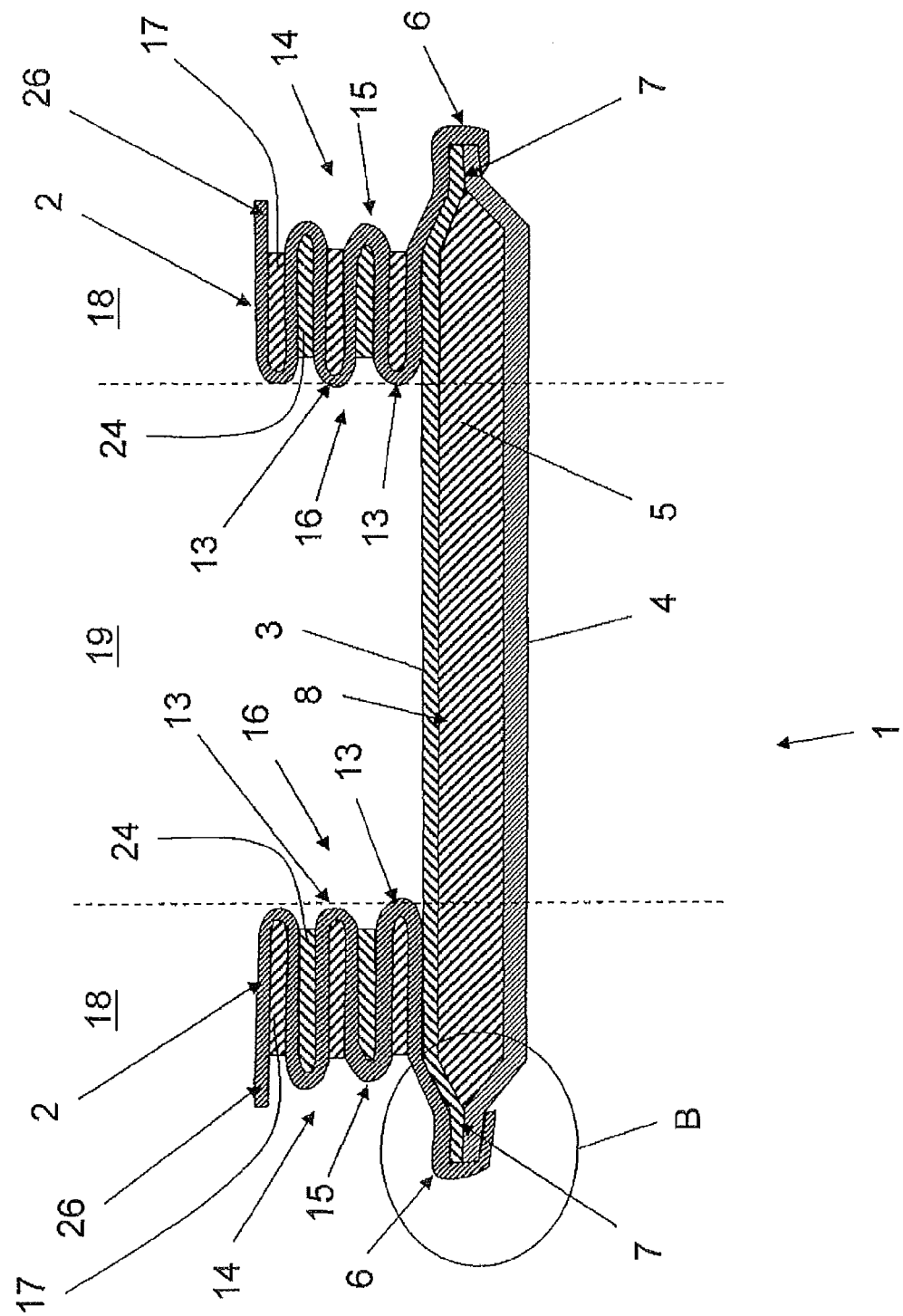
FIG. 4 schematically shows a cross-sectional view along line A-A in FIG. 1.

FIG. 4 schematically shows a cross-sectional view along line A-A in FIG. 1. FIG. 4 shows that each fastening tab 2 is folded over itself five times creating three first pleats 13 on the first side 14 of the fastening tabs 2 and two second pleats 15 on the second side of the fastening tab 2.

The first pleats 13 comprise fastening means 17 and, as been described above, at least one of the first pleats 13 may have a different adherent strength than a fastening means 17 of another first pleat 13 giving the fastening tab 2 a selective and stepwise unfolding of the different pleats 13, 15.

In FIG. 4, the second pleats 15 comprise an additive 24. The additive 24 may be a skincare lotion and/or an odour inhibitor, and/or an absorption layer and/or a perfume and/or any other suitable additive.

In FIG. 4 it is shown that the fastening tabs 2 are folded over the side sections 18 on the topsheet 3 of the absorbent article forming side leakage barriers 25. When the absorbent article 1 is positioned for use with the fastening tabs 2 in the first position as shown in FIG. 4, the fastening tabs form raised side leakage barriers 25 that hinder fluid from flowing over the side edges 6. When the absorbent article 1 comprises only an absorbent body 5 and a backsheet 4, the fastening tabs 2 are folded over the side sections 18 on the absorbent body 5 of the absorbent article 1 forming the side leakage barriers 25. The fastening tabs 2 may be unfolded only partly, leaving a part of the fastening tabs 2 in a folded state forming side leakage barriers 25 according to the above.

The fastening tabs 2 may also comprise gripping means 26 that the user can hold when arranging the fastening tabs 2 into a desired position or shape. The gripping means 26 may be a small integrated portion of the fastening tab or may be a separate sheet attached to the fastening tabs.

Figure 5:
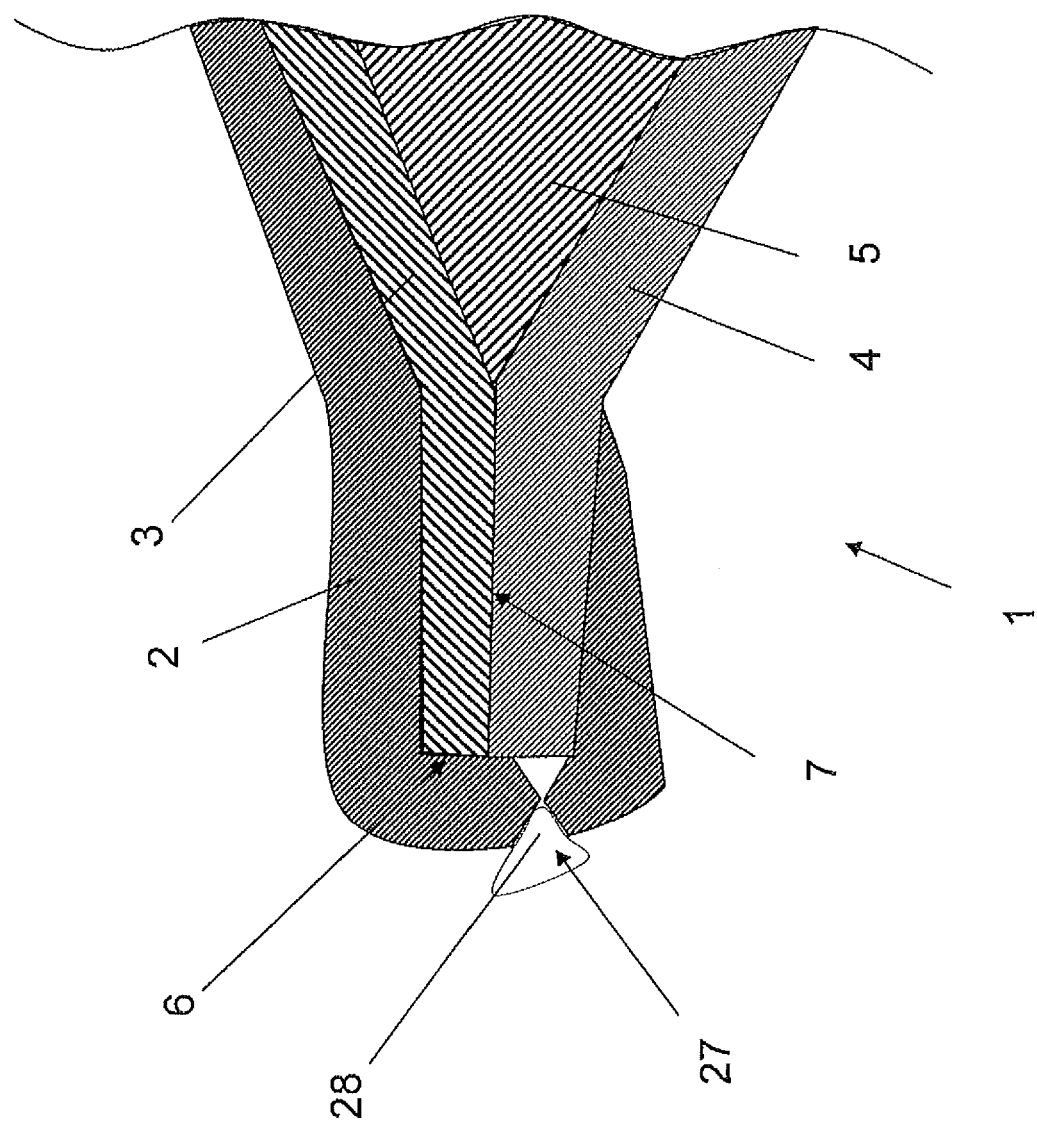
FIG. 5 schematically shows an enhanced section B in FIG. 4 according to one embodiment of the invention.

FIG. 5 schematically shows an enhanced section B in FIG. 4 according to one embodiment of the invention. In FIG. 5, the fastening tabs 2 are detachably attached to the backsheet 4 of the absorbent article 1. The fastening tab 2 comprises a tear line 27 comprising weakened zones 28. The tear line 27 may comprise any types of compressed parts, indentations, removed parts or apertures arranged to weaken the tear line for allowing separation of the fastening tabs 2 from the absorbent article 1.

Figure 6:
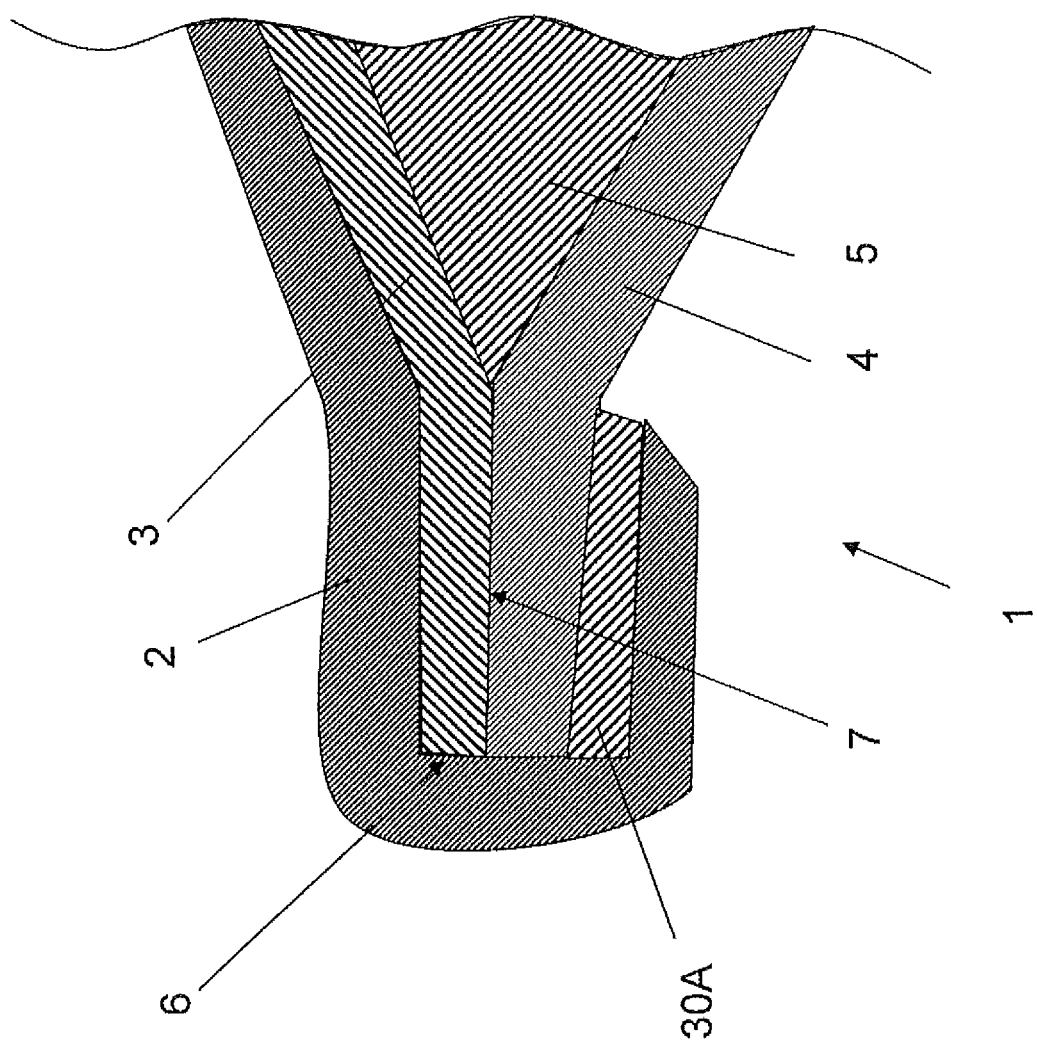
FIG. 6 schematically shows an enhanced section B in FIG. 4 according to another embodiment of the invention.

FIG. 6 schematically shows an enhanced section B in FIG. 4 according to another embodiment of the invention. FIG. 6 shows that the fastening tabs 2 are detachably attached to the absorbent article 1. The fastening tabs 2 are detachably attached to the backsheet 4 of the absorbent article. The fastening tabs 2 may be detachably attached to the absorbent article 1 via an adhesive 30A.

Figure 7:
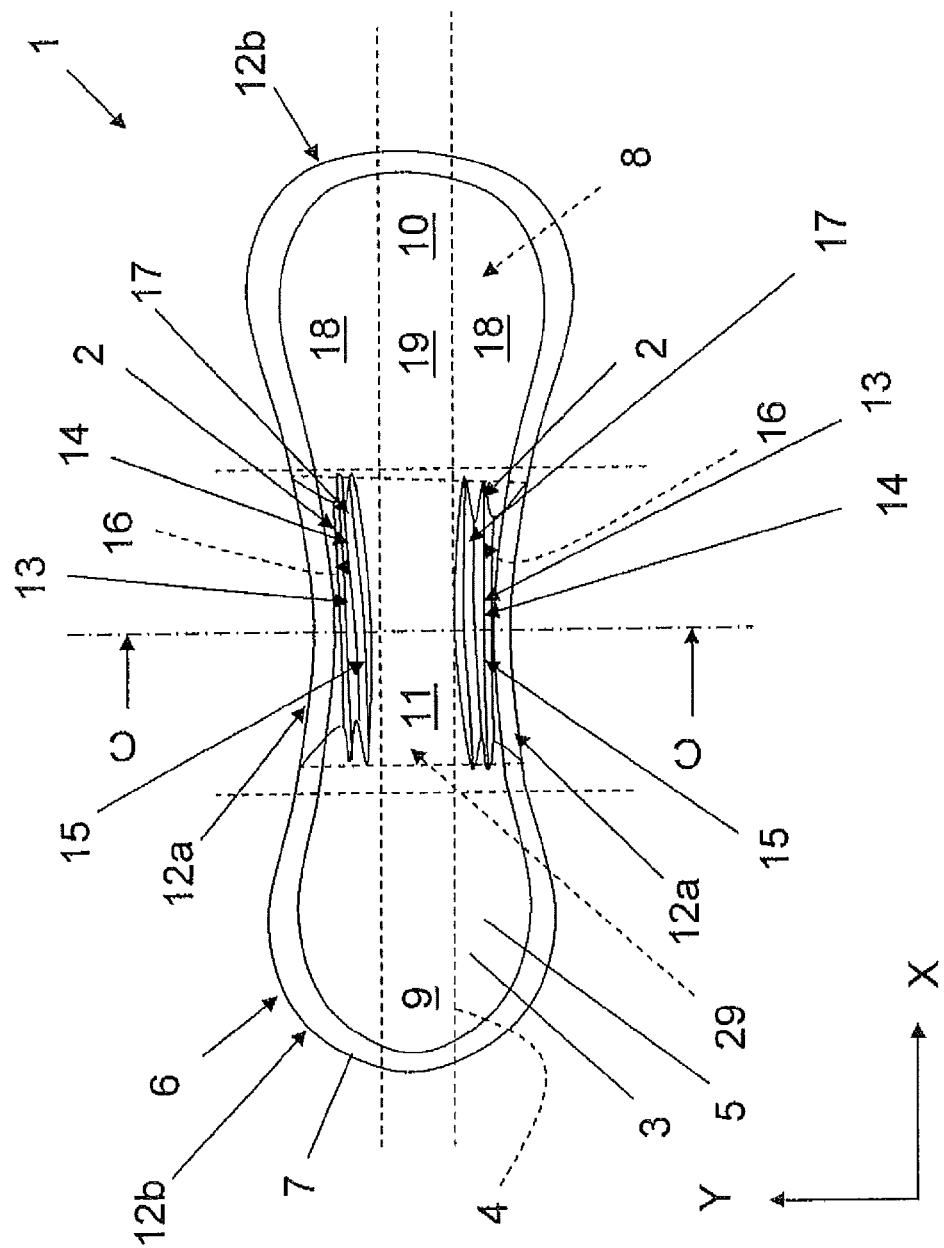
FIG. 7 schematically shows a top view of an absorbent article according to a second embodiment of the invention.

FIG. 7 schematically shows a top view of an absorbent article 1 according to a second embodiment of the invention. In FIG. 7, the fastening tabs 2 are comprised in one tab sheet 29 extending over the backsheet 4 of the absorbent article 1. The tab sheet 29 may be fixedly attached to the backsheet 4 or the tab sheet 29 may be an extension of the backsheet 4 or the tab sheet 29 may be detachably attached to the backsheet 4 of the absorbent article 1. In the latter case the fastening tabs 2, i.e. the tab sheet 29, may be detachably attached to the absorbent article 1 via an adhesive.

The tab sheet 29 may comprise a tear line (not shown) according to FIG. 5. The tab sheet 29 may thus comprise compressed zones, indentations or apertures arranged to weaken the tear line for allowing separation of the fastening tab 2 from the absorbent article.

The invention is not limited to one tab sheet 29, but a number of tab sheets 29 may be arranged on the backsheet. If two or more tab sheets are used, more complex geometries can be achieved, for example an X-shape. Two or more tab sheets can give a number of fastening tabs positioned on different locations along the longitudinal side edge. Furthermore, one tab sheet may have a more complex form than just being essentially rectangular and may comprises a number of fastening tabs.

Figure 8:
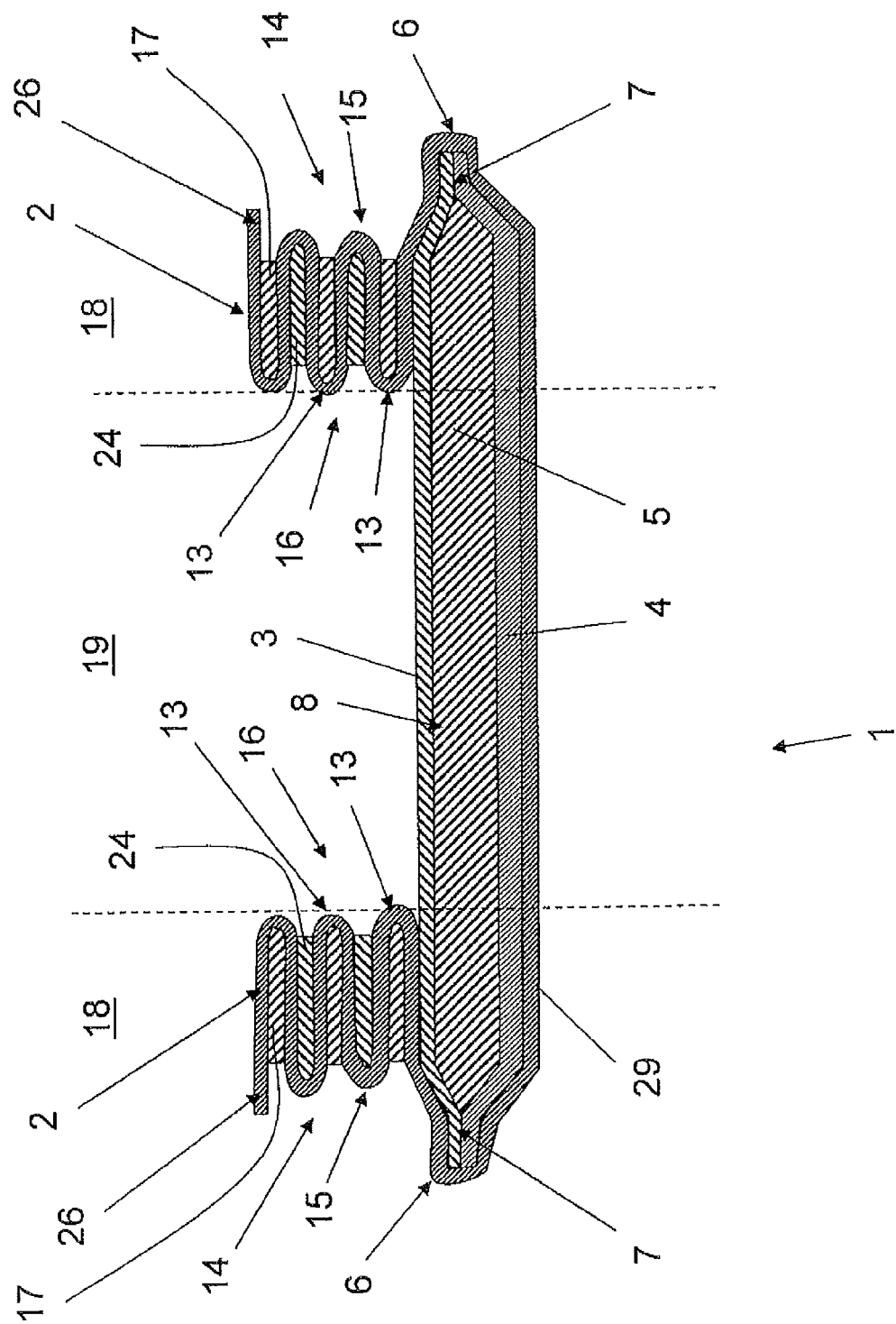
FIG. 8 schematically shows a cross-sectional view along line C-C in FIG. 7 according to one embodiment of the invention.

FIG. 8 schematically shows a cross-sectional view along line C-C in FIG. 7 according to one embodiment of the invention. FIG. 8 shows an embodiment where the tab sheet 29 is fixedly attached to the backsheet 4 of the absorbent article 1.

Figure 9:
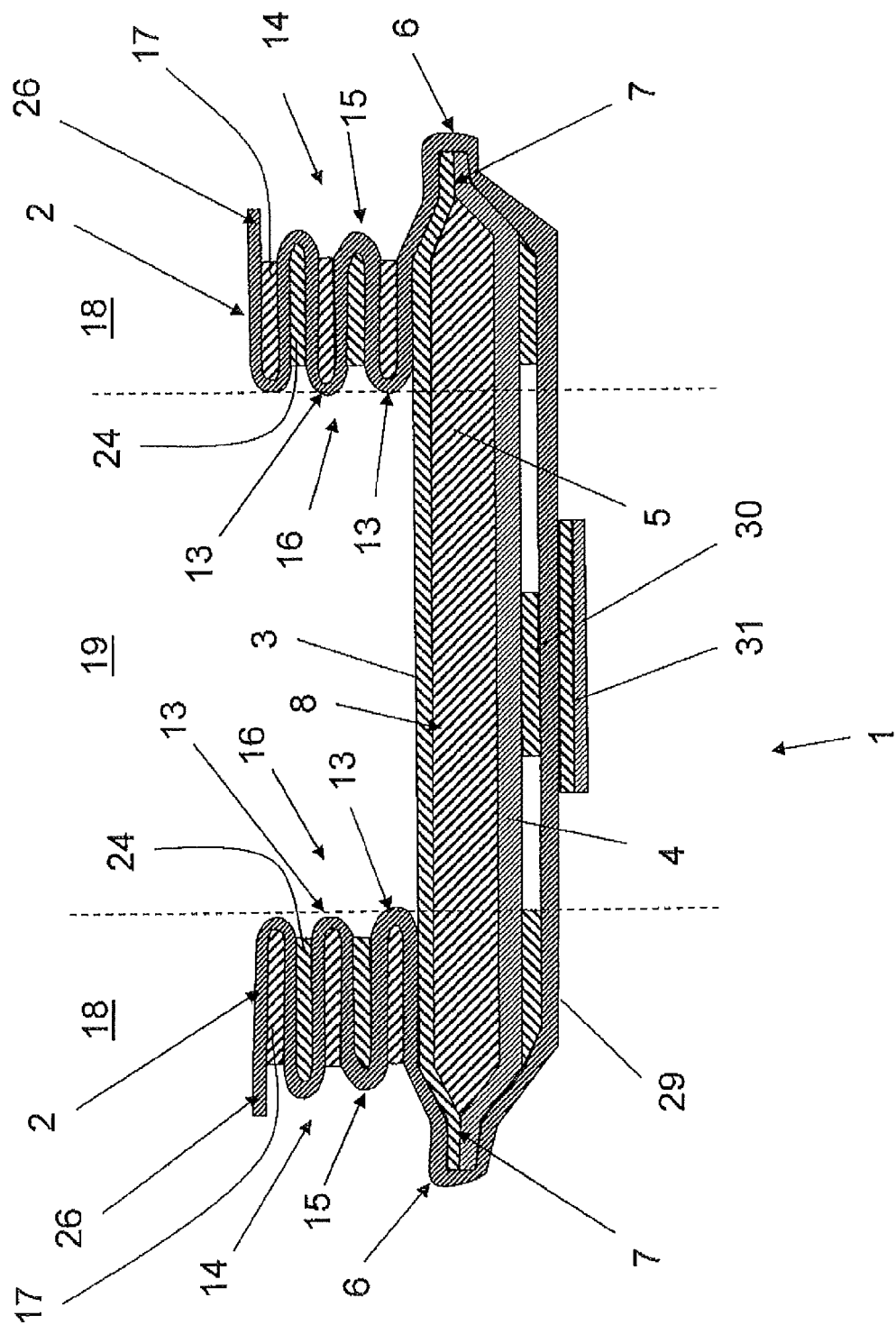
FIG. 9 schematically shows a cross-sectional view along line C-C in FIG. 7 according to another embodiment of the invention.

FIG. 9 schematically shows a cross-sectional view along line C-C in FIG. 7 according to another embodiment of the invention. In FIG. 9, the tab sheet 29 is arranged as a release sheet for a first adhesive strip 30 positioned on the backsheet 4 so that the first adhesive strip 30 is revealed should the tab sheet 29 be removed. In FIG. 8, the tab sheet 29 comprises a second adhesive strip 31 positioned on the opposite side of the tab sheet 29 in relation to the first adhesive strip 30. The second adhesive strip 31 is used for securing the absorbent article 1 in an undergarment if the tab sheet 29 is not removed and the first adhesive strip 30 is used if the tab sheet 29 is removed. The second adhesive strip 31 can be opt out since the fastening tabs 2 are arranged for securing the absorbent article 1 to the undergarment.

Figure 10:
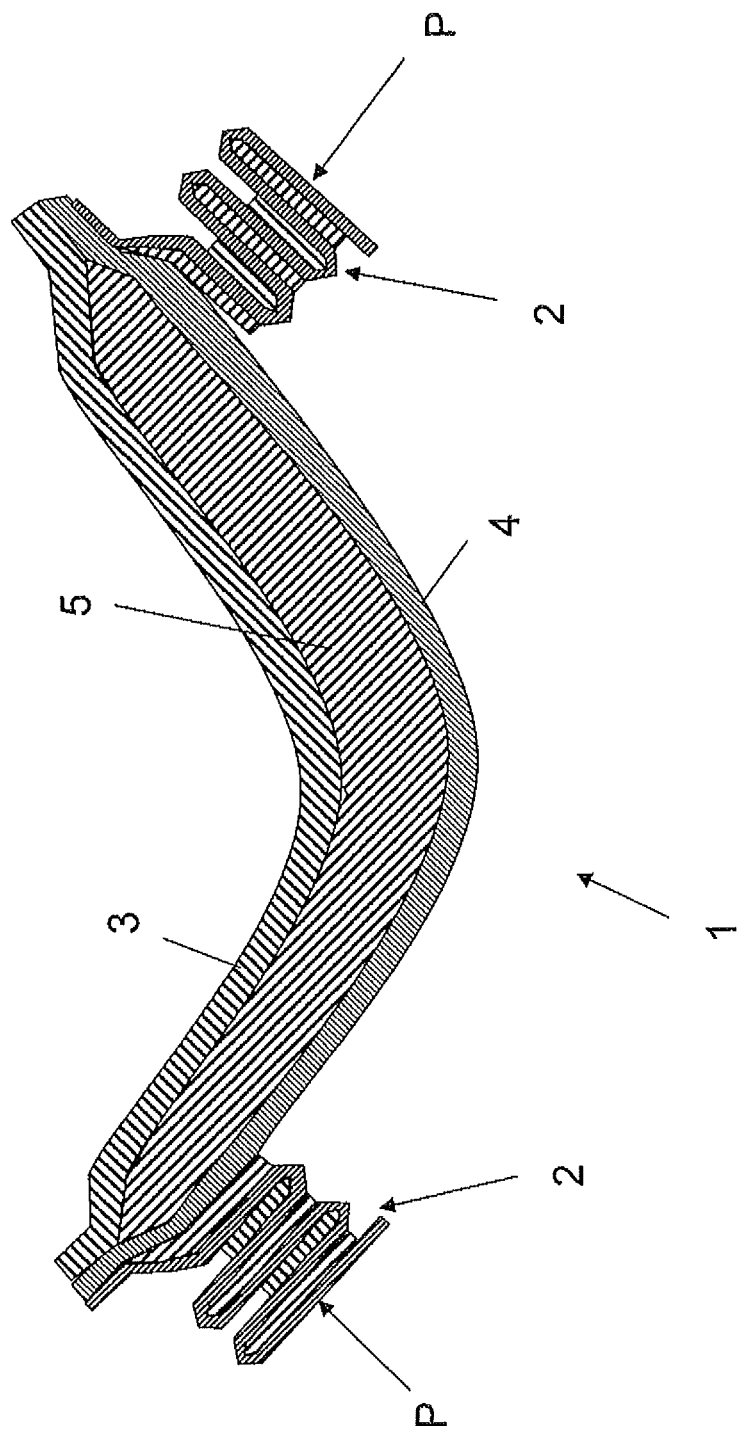
FIG. 10 schematically shows a cross-sectional view along line A-A in FIG. 1 when the absorbent article is bent for use.

FIG. 10 schematically shows a cross-sectional view along line A-A in FIG. 1 when the article is bent for use. FIG. 10 shows that the fastening tabs 2 are folded over the backsheet 4 in the side sections 18 in the first position. The pleated fastening tabs 2 indirectly form side leakage barriers by pushing the material in the absorbent article 1 in direction towards the midsection 19 of the absorbent article 1 during use. In FIG. 10, the absorbent article 1 is shown somewhat bent in order to explain how the absorbent article is formed between the legs of a user when in use. In FIG. 10, "the direction" is shown with arrows P. The "pushing" is a consequence of the user's body pushing onto the pleated fastening tabs 2 during use since the pleated fastening tabs 2 will be positioned between the undergarment and the absorbent article. In one embodiment of the invention, the fastening tabs are only partly unfolded, i.e. a part of the fastening tabs remains in the first position (i.e. in a folded position) and the unfolded parts in the second position are used for fastening the absorbent article in the undergarment.

FIG. 11 schematically shows a top view of an absorbent article 1 according to a third embodiment of the invention. FIG. 11 shows that the two fastening tabs 2 are in an unfolded state, but that they have different appearances. One of the fastening tabs 2, denoted F1, has a round shape and the other fastening tab 2, denoted F2, has a more triangular and pointy shape. The fastening tabs 2 comprise first zones 32 with different elastic properties than second zones 33. The fastening tabs also comprise reinforcement zones 34 that aid the user in forming the fastening tab F1 into the shape of fastening tab F2. This has also been explained in connection to FIG. 2. FIG. 11 shows that the first zone 32 is more elastic than the second zone 33 and that the fastening tab 2 therefore changes shape from F1 to F1, with the aid of the reinforcement zones 34, when the fastening tabs 2 are subject to an external force. The reinforcement zones 34 aid in the shaping since they more or less maintains their shape when the fastening tab is subject to external forces.

It should be noted that the zones 32, 33, 34 for shaping may be comprised in all embodiments of the invention and is not limited to the embodiments described above in connection to FIGS. 1-10.

In FIG. 11 the fastening tabs 2; F1, F2 are positioned along the longitudinally extending side edges 12a, and partly in the front portion 9 and partly in the central portion 11. The fastening tabs 2; F1; F2 are arranged to be folded over the side edges of an undergarment. The fastening tabs comprise fastening means 17 arranged on the first side 14 of the fastening means and arranged to be attached on the outside of an undergarment. In FIG. 11 the absorbent article 1 is positioned with the backsheet 4 facing a reader.

FIG. 11 shows that the absorbent article 1 comprises second fastening tabs 2; 35 arranged along the longitudinal side edges 12a. In FIG. 11 the second fastening tabs 2; 35 are positioned partly in the rear portion 10 and partly in the central portion 11. However, the second fastening tabs 2; 35 could be positioned in the front portion 9 or in the rear portion 10. The second fastening tabs 2; 35 could also be positioned along the laterally extending side edges 12b. The second fastening tabs 2; 35 may be arranged in the same manner as the fastening tabs 2 described above. Hence, the second fastening tabs 2; 35 may be folded over itself so that pleats are created and may be stored folded in a first position and being arranged to be partly or wholly unfolded into a second position. The second fastening tabs 2; 35 may also comprise first zones, second zones and reinforcement zones. The second fastening tabs 2; 35 may comprise second fastening means 17b for attachment in the undergarment. The second fastening means 17b may be arranged to be attached to the inside or the outside of the undergarment. In FIG. 11 the second fastening tabs 2; 35 are shown in the second position, i.e. in their unfolded state, i.e. in their un-pleated state. The second fastening tabs 2; 35 may be arranged to be folded over the side edge of the undergarment and/or may be arranged to be attached in the undergarment when being in the second position.

FIG. 11 shows that the absorbent article comprises a third fastening tab 2; 36 positioned in the front portion 9 along the laterally extending side edge 12b. The third fastening tab 2; 36 may be arranged in an identical manner as the fastening tab positioned 2 along the longitudinal side edge and the second the fastening tab. The third fastening tab may also be positioned in the rear portion 10 and the absorbent article 1 may comprise two opposing third fastening tabs 2; 36 positioned in the front portion 9 and the rear portion 10 respectively. The third fastening tab 2; 36 may comprise fastening means arranged to be attached to the outside or the inside of an undergarment. In FIG. 11 the third fastening tab 2; 36 is in the first position, i.e. in its folded state, but can be unfolded into the second position for attachment to the inside and/or the outside of an undergarment.

One advantage of the invention is that the fastening tab can have an aesthetically pleasing shape in the first position and a functionally perfect shape in the second position. A further advantage is that the pleat gives the possibility to arrange the fastening tab so that the user can arrange the fastening tabs in a number of different ways by manipulating the fastening tabs. Examples of this will be apparent in the below description of the invention.

The invention thus relates to an improved absorbent article comprising at least one fastening tab positioned along the side edge 6 for attachment to the outside and/or the inside of an undergarment.

Figure 12:
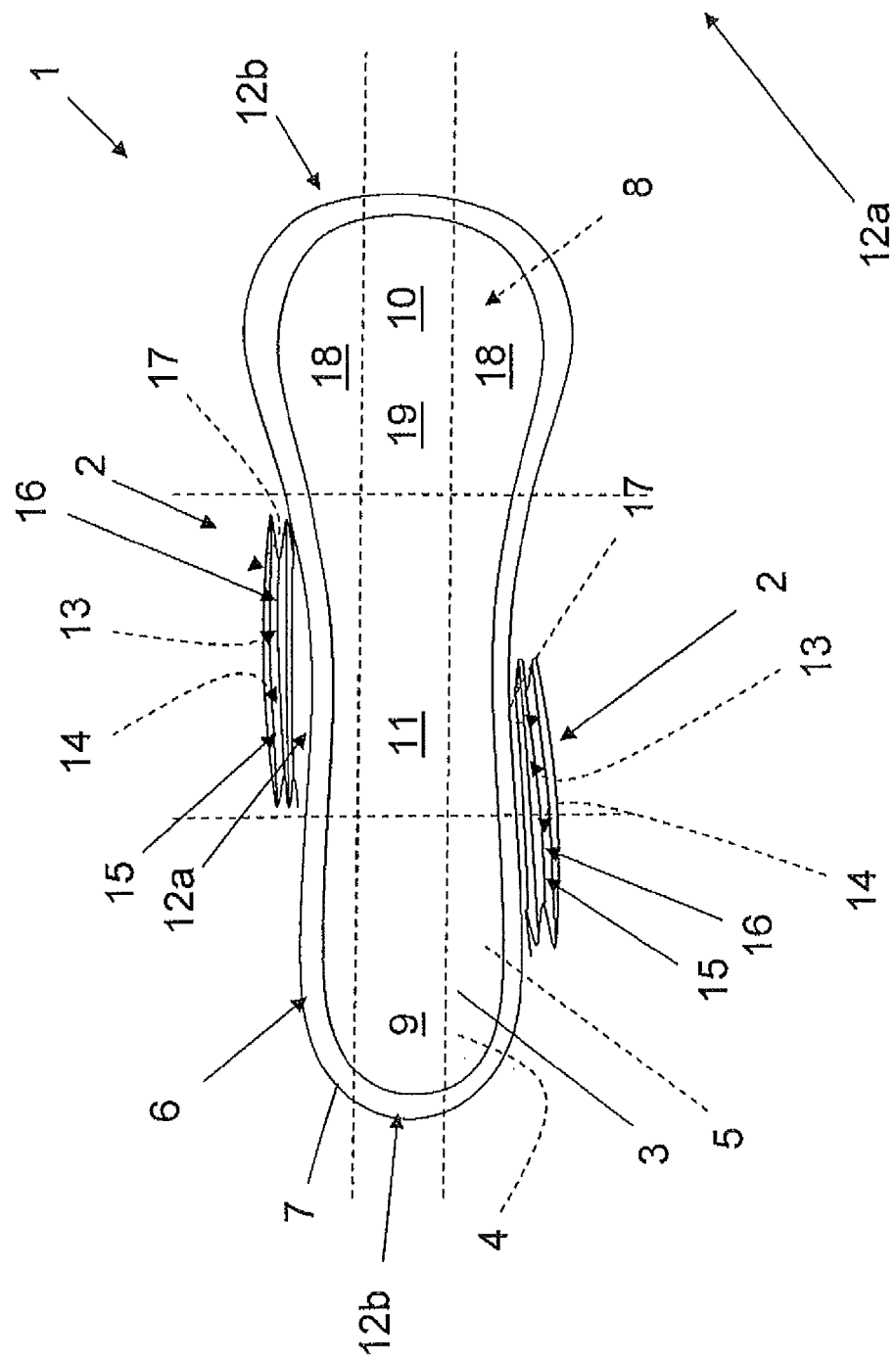
FIG. 12 schematically shows a top view of an absorbent article according to a fourth embodiment of the invention.

FIG. 12 schematically shows a top view of an absorbent article according to a fourth embodiment of the invention. The fastening flaps 2 in FIG. 12 are similar to the fastening flaps 2 in FIGS. 1-11 with regard to their construction. In FIG. 12 the absorbent article 1 comprises two fastening tabs 2 positioned on either side of the absorbent article 1 along the longitudinally extending side edges 12a for improved fastening abilities. One of the fastening tabs 2 is positioned in the central portion 11 and the other fastening tab 2 is positioned partly in the front portion 9 and partly in the central portion 11. Hence, the fastening flaps 2 are not positioned opposite each other with regard to a longitudinally extending center axis (not shown), but are positioned in a diagonal pattern with reference to the longitudinally extending center axis. However, the fastening tabs could be positioned completely in the front portion 9 or the rear portion 10 or the central portion 11, or partly in either of them. In FIG. 12 the fastening tabs are shown in the first position, i.e. in a folded state. The fastening tabs 2 are not folded over the side edge 6 of the absorbent article, but are positioned in the same plane as described by the absorbent article. Hence, the fastening flaps 2 are positioned adjacent the absorbent article. The attachment of the fastening flaps to the absorbent article can be done in any of the ways descried in connection to any of FIG. 1-11 or a combination thereof.

Figure 13:
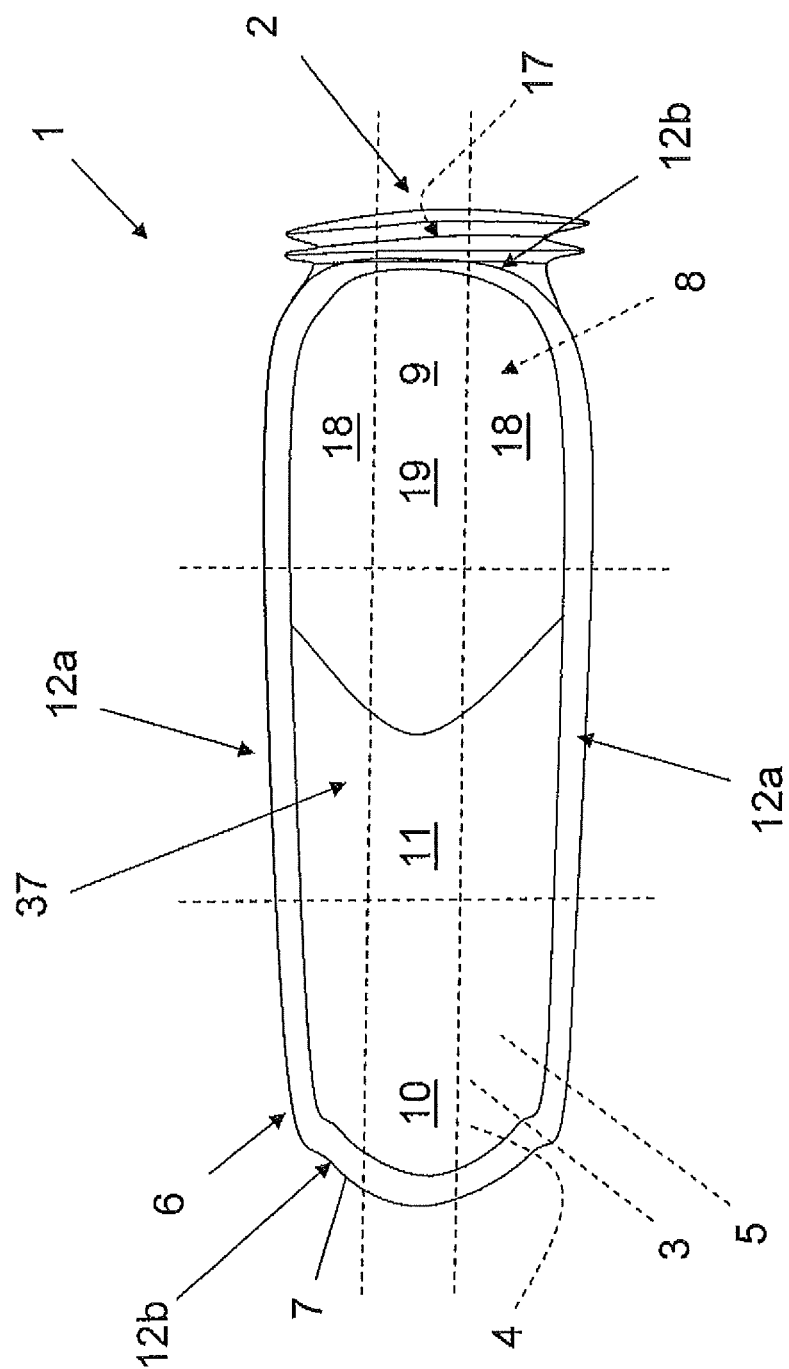

FIG. 13 schematically shows a top view of an absorbent article according to a fifth embodiment of the invention. FIG. 13 shows one fastening tab 2 being positioned in the front portion 9 along the laterally extending side edge 12b. FIG. 13 shows the fastening flap 2 in the first position. The user may after insertion of the absorbent article 1 into an undergarment bring the fastening flap 2 from the first position into the second position and may then attach the fastening flaps 2 on the outside and/or on the inside of the undergarment.

The arrangement shown in FIG. 13 is advantageous for use as an incontinence article in a men's undergarment. FIG. 13 shows that a pouch 37 is positioned over the topsheet 3 of the absorbent article. The pouch 37 is arranged to accommodate the user's penis. The pouch 37 is advantageously water tight so that bodily exudates emanating from the penis is trapped in the pouch 37 and absorbed by the absorbent article 1.

Figure 14:
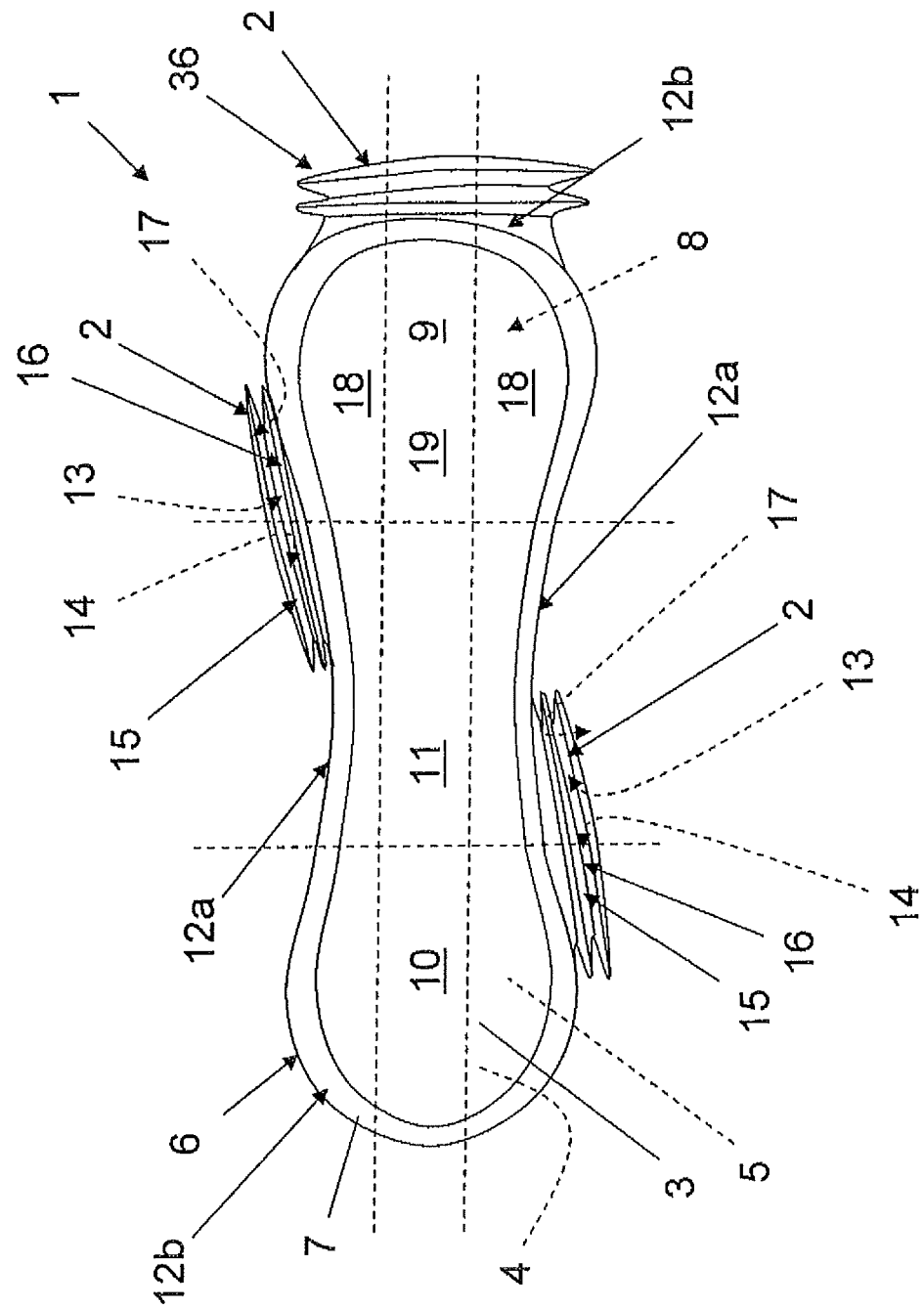
FIG. 14 schematically shows a top view of an absorbent article according to a sixth embodiment of the invention.

FIG. 14 schematically shows a top view of an absorbent article according to a sixth embodiment of the invention. FIG. 14 shows a combination of FIGS. 12 and 13 with regard to the position of the fastening tabs 2, 36, but with the difference that one of the fastening tabs 2 is positioned partly in the rear portion 10 and partly in the central portion 11 whereas the other fastening tab 2 is positioned partly in the front portion 9 and partly in the central portion 11 However, all embodiments described in FIGS. 1-13 may be combined so that there are at least one fastening tab 2 attached along the longitudinally extending side edges 12a and at least one fastening tab 2; 36 attached to one of the laterally extending side edges 12b. The fastening tabs may then optionally be unfolded by the user dependent on personal preferences.

The invention claimed is:

1. An absorbent article comprising an absorbent body arranged superpositioned onto a backsheet, the absorbent article having an extension in a longitudinal direction and a lateral direction, the absorbent article having a front portion, a rear portion and a central portion therebetween, the absorbent article having a side edge at a periphery of the absorbent article, the absorbent article comprising at least one fastening tab positioned along the side edge, wherein the fastening tab, in a first position, is folded over itself at least two times creating at least one first pleat on a first side of the fastening tab and at least one second pleat on a second side of the fastening tab, the fastening tab being secured in its folded position by fastening means positioned in the first pleat on only the first side of the fastening tab, and in a second position, the fastening tab is arranged to be unfolded at least partly such that the fastening means can attach to an undergarment, and wherein the second pleat comprises an additive.

2. An absorbent article according to claim 1, wherein the fastening tab is folded over itself at least three times creating at least two first pleats on the first side of the fastening tab and at least one second pleat on the second side of the fastening tab.

3. An absorbent article according to claim 2, wherein at least one of the first pleats comprises a fastening means with a different adherent strength than a fastening means of another first pleat giving the fastening tab a selective and stepwise unfolding of the different pleats.

4. An absorbent article according to claim 1, wherein the absorbent article, in the lateral direction, is divided into two side sections and a mid section therebetween, wherein the fastening tab is folded over the side section forming a side leakage barrier.

5. An absorbent article according to claim 1, wherein the fastening tab is folded over the backsheet side of the absorbent article or is folded over the absorbent body side of the absorbent article with relation to the backsheet.

6. An absorbent article according to claim 1, wherein the fastening tab comprises a first zone and a second zone having different properties for shaping the fastening tab when the fastening tab is brought from the first position to the second position.

7. An absorbent article according to claim 6, wherein the first zone and the second zone have different elastic properties.

8. An absorbent article according to claim 6, wherein the first zone is permanently or plastically deformable.

9. An absorbent article according to claim 6, wherein the second zone has different properties from the first zone.

10. An absorbent article according to claim 1, wherein the fastening tab is comprised in one tab sheet extending over the backsheet of the absorbent article.

11. An absorbent article according to claim 10, wherein the tab sheet is arranged as a release sheet for a first adhesive strip positioned on the backsheet for revealing the first adhesive strip should the tab sheet be removed.

12. An absorbent article according to claim 11, wherein the tab sheet comprises a second adhesive strip positioned on the opposite side of the tab sheet in relation to the first adhesive strip.

13. An absorbent article according to claim 1, wherein the fastening tab is fixedly attached to the absorbent article.

14. An absorbent article according to claim 13, wherein the fastening tab is fixedly attached to the backsheet.

15. An absorbent article according to claim 1, wherein the fastening tab is an extension of the backsheet.

16. An absorbent article according to claim 1, wherein the fastening tab comprises a tear line arranged to weaken the fastening tab for allowing separation of the fastening tab from the absorbent article.

17. An absorbent article according to claim 1, wherein the fastening tab comprises a reinforcement zone arranged to shape the fastening tab when the fastening tab is brought from the first position to the second position.

18. An absorbent article according to claim 1, wherein the absorbent article comprises a topsheet arranged superpositioned onto the absorbent body.

19. An absorbent article according to claim 1, wherein at least one fastening tab is positioned in the front portion or the rear portion or the central portion or at a position therebetween.

20. An absorbent article according to claim 19, wherein the fastening tab is positioned along a longitudinally extending side edge.

21. An absorbent article according to claim 1, wherein the absorbent article comprises at least two fastening tabs.

22. An absorbent article according to claim 21, wherein at least two fastening tabs are positioned on either side of the absorbent article along the longitudinally extending side edges.

23. An absorbent article according to claim 1, wherein the fastening tab is arranged to be unfolded at least partly for attachment to the outside or the inside of an undergarment by the fastening means.

24. An absorbent article according to claim 1, wherein the additive is at least one of a skincare lotion and a perfume.

25. An absorbent article according to claim 1, wherein the additive is an absorption layer.

\* \* \* \* \*